United States Patent [19]

Maignan et al.

[11] Patent Number: 5,023,363

[45] Date of Patent: Jun. 11, 1991

[54] AROMATIC COMPOUNDS, A PROCESS FOR THEIR PREPARATION AND THEIR USE IN HUMAN AND VETERINARY MEDICINE AND FOR COSMETIC COMPOSITIONS

[75] Inventors: Jean Maignan, Tremblay-les-Gonesse; Gérard Lang, Saint-Gratien; Gérard Malle, Villiers-sur-Morin; Serge Restle, Aulnay-sous-Bois; Braham Shroot, Antibes, all of France

[73] Assignee: L'Oreal, Paris, France

[21] Appl. No.: 176,746

[22] Filed: Apr. 1, 1988

Related U.S. Application Data

[63] Continuation of Ser. No. 33,690, Apr. 3, 1987.

[30] Foreign Application Priority Data

Apr. 4, 1986 [LU] Luxembourg .......................... 86387

[51] Int. Cl.$^5$ ............................................. C07C 69/76
[52] U.S. Cl. ....................................... 560/52; 560/21; 560/56; 562/466; 562/460; 562/461; 562/462; 544/391; 544/176; 546/205; 546/206; 548/530; 536/48; 536/45
[58] Field of Search .......................... 560/52, 21, 56; 562/460, 461, 462, 466; 544/391, 176; 546/205, 206; 548/530; 536/48, 45

[56] References Cited

PUBLICATIONS

Royals, E. Earl, "Adv. Org. Chem.", p. 581, Prentice-Hall, Inc., 1959.
Chemical Abstracts, CA 98(21):178842n, 1983.

*Primary Examiner*—Paul J. Killos
*Attorney, Agent, or Firm*—Cushman, Darby & Cushman

[57] ABSTRACT

An aromatic compound of the formula

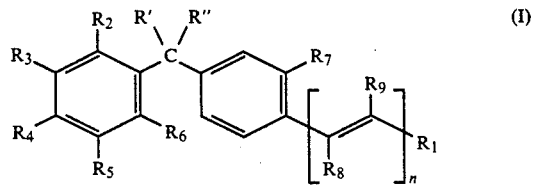

(I)

These compounds are useful in human and veterinary medicines and in cosmetic compositions.

22 Claims, No Drawings

AROMATIC COMPOUNDS, A PROCESS FOR THEIR PREPARATION AND THEIR USE IN HUMAN AND VETERINARY MEDICINE AND FOR COSMETIC COMPOSITIONS

This is a continuation of application Ser. No. 033,690, filed Apr. 3, 1987.

BACKGROUND OF THE INVENTION

The present invention relates to new aromatic compounds, to a process for their preparation and to their use in human and veterinary medicine and in cosmetic compositions.

The compounds in accordance with the present invention exhibit an activity in the topical and systemic treatment of dermatologic diseases linked to a keratinization disorder (differentiation-poliferation) and dermatologic diseases (or others) having inflammatory and/or immunoallergic components and in the treatment of illnesses of the degeneration of conjunctive tissue as well as an anti-tumoral activity. Moreover, these compounds can be employed in the treatment of atophy, be it cutaneous or respiratory and in the treatment of rheumatoid psoriasis.

These compounds also possess good activity against the germs involved in acne.

Finally, the compounds of the present invention are usefully employed in the opthamology field and principally in the treatment of corneopathies.

The aromatic compounds of the present invention can be represented by the formula:

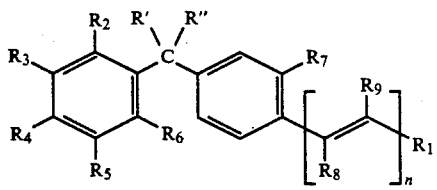

wherein
n is 0 or 1,
(1) when n=1,
R' represents hydrogen or alkoxy having 1–4 carbon atoms,
R" represents hydrogen, OH, acyloxy having 1–4 carbon atoms, alkoxy having 1–4 carbon atoms or $NH_2$,
or R' and R" taken together form an oxo (=O), methano ($-CH_2$) or hydroxy imino (=N—OH) group,
$R_1$ represents $-CH_2OH$ or $-COR_{10}$,
$R_{10}$ represents hydrogen, $-OR_{11}$ or

$R_{11}$ represents hydrogen, linear or branched alkyl having 1–20 carbon atoms, monohydroxalkyl, polyhydroxyalkyl, aryl or aralkyl optionally substituted, the residue of a sugar or

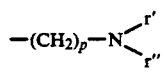

wherein p is 1, 2 or 3 and r' and r" represent hydrogen, lower alkyl, monohydroxyalkyl optionally interrupted by a heteroatom, polyhydroxyalkyl, aryl or benzyl optionally substituted, the residue of an amino acid or aminated sugar, or taken together form a heterocycle, $R_2$, $R_3$, $R_4$, $R_5$ and $R_6$ represent hydrogen, —OH, linear or branched alkyl having 1–12 carbon atoms, cycoalkyl, cycloalkenyl, phenyl optionally substituted or a radical corresponding to one of the following formulas:

(i) $-X-C_6H_5$,
(ii) $-X-R_{12}$ or
(iii) $-NHCOR_{13}$ wherein
X represents —O—, —S—, —SO—, —$SO_2$— or —OCO—,
$R_{12}$ represents alkyl or lower fluoroalkyl, and
$R_{13}$ represents alkyl or phenyl, at least one of $R_2$ to $R_6$ being other than hydrogen,
$R_7$, $R_8$ and $R_9$ represent hydrogen or methyl, $R_7$ and $R_9$ taken together being able to form, with the benzene ring, a naphthalene ring, with the exclusion of compounds of formula (I) wherein $R_7$ is hydrogen or methyl when $R_4$ represents methyl or OH, when $R_2$, $R_3$, $R_5$ and $R_6$ represent hydrogen or when $R_6$ represent hydroxyl;
(2) when n=0
R' represents hydrogen,
R" represents OH, or
R' and R" taken together form an oxo (=O) radical,
$R_1$ represents $-CH_2OH$, $-CH=O$ or $-COOR_{11}$ wherein $R_{11}$ is hydrogen or lower alkyl,
$R_2$ and $R_3$ represent hydrogen or alkyl having 3–6 carbon atoms,
$R_5$ represents
(i) either cycloalkyl or alkyl having 3–6 carbons atoms and in this case $R_4$ represents lower alkyl, hydroxy or alkoxy, or
(ii) hydrogen and in this case $R_4$ represents lower alkyl,
$R_6$ represents hydrogen and
$R_7$ represents hydrogen or methyl,
and the salts of said aromatic compounds as well as their optical and geometric isomers.

By lower alkyl is meant an alkyl radical having 1–6 carbon atoms.

Representative lower alkyl radicals and those having up to 20 carbon atoms include methyl, ethyl, isopropyl, butyl, tert.butyl, isooctyl, dodecyl, hexadecyl and octadecyl.

By monohydroxyalkyl is meant a radical having 2–6 carbon atoms and principally 2-hydroxyethyl, 2-hydroxypropyl or 2-hydroxy ethoxyethyl.

By polyhydroxyalkyl is meant a radical containing 3–6 carbon atoms and 2–5 hydroxyl groups such as 2,3-dihydroxypropyl, 1,3-dihydroxypropyl or the residue of pentaerythritol.

By aryl is meant phenyl optionally substituted by halogen, —OH, —$NO_2$, lower alkyl, trifluoromethyl or a carboxylic acid function.

The preferred aralkyl radical is benzyl or phenethyl.

By residue of a sugar is meant a residue derived, for example, from glucose, mannose, erythrose or galactose.

By residue of an amino acid is meant a residue derived, for example, from methionine or α- or β-alanine.

Representative residues of aminated sugars include those derived from glucosamine, galactosamine or mannosamine.

By cycloalkyl is meant radicals having from 5–12 carbon atoms and principally cyclopentyl, cyclohexyl and adamantyl.

By cycloalkenyl is meant, preferably, cyclohexen-1-yl and cyclopenten-1-yl.

The preferred fluoroalkyl radicals are trifluoromethyl and pentafluoroethyl.

When the radicals r' and r" taken together from a heterocycle, the heterocycle is, preferably, piperidino, piperazino, morpholino, pyrrolidino or 4-(2-hydroxyethyl) piperazino.

When the compounds according to the present invention are provided in the form of salts, they can be salts of an alkali or alkaline earth metal or even of zinc, or of an organic amine when they carry at least one free acid function, or of salts of a mineral organic acid, principally the hydrochloride, hydrobromide or citrate when they carry at least one amine function.

As a function of formula (I) above, the compounds of the present invention can be benzene derivatives or naphthalene derivatives of following formulas (II) and (III):

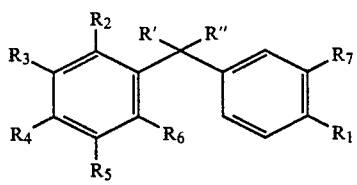

wherein $R_1$ to $R_7$, R' and R" have the same meanings given for those in formula (I) when n=0,

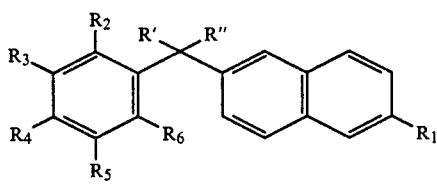

wherein $R_1$ to $R_6$, R' and R" have the same meanings given for those in formula (I) when n=1.

It will be noted that the compounds of formula (III) have good stability to light and oxygen.

Among the compounds of formula (II) those particularly preferred correspond to following formula (IV):

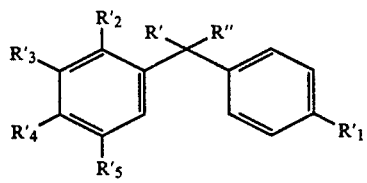

wherein

R' represents hydrogen,

R" represents OH or

R' and R" taken together from an oxo (=O) radical, $R'_1$ represents —CH$_2$OH, —CH=O or —COOR'$_{11}$ wherein R'$_{11}$ is hydrogen or lower alkyl, $R'_2$ and $R'_3$ represent hydrogen or alkyl having 3–6 carbon atoms, and $R'_5$ represents either (i) cycloalkyl or alkyl having 3–6 carbon atoms and in this case $R'_4$ represents lower alkyl, hydroxy or alkoxy, or (ii) hydrogen and in this case $R'_4$ represents lower alkyl.

Among the compounds of formula (III) those particularly preferred correspond to following formulas (V) and (VI):

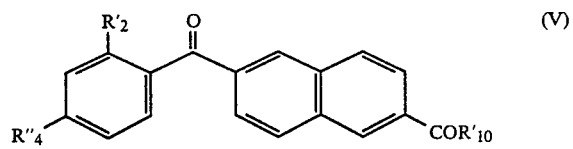

wherein $R'_{10}$ represents —OR'$_{11}$ or —NHR'$_{11}$ wherein R'$_{11}$ represents hydrogen or lower alkyl, $R'_2$ represents hydrogen or lower alkyl, and $R'_4$ represents lower alkyl, preferably isopropyl or tert.butyl, or cycloalkyl, preferably, cyclohexyl.

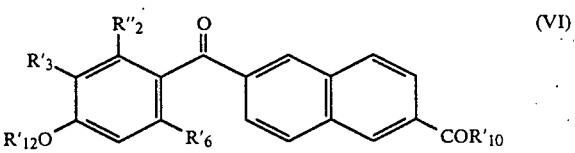

wherein $R'_{10}$ represents —OR'$_{11}$ or —NHR'$_{11}$ wherein R'$_{11}$ represents hydrogen or lower alkyl, R"$_2$ and R'$_6$ represent hydrogen or lower alkyl, $R'_3$ represents hydrogen, lower alkyl, phenyl or adamantyl, and $R'_{12}$ represents lower alkyl or phenyl.

Representative compounds of formula (I) in accordance with the present invention include the following:

(1) 6-(2,4-diisopropyl benzoyl) 2-methyl naphthalene carboxylate, (2) 6-(2,4-diisopropyl benzoyl) naphthalene carboxylic acid, (3) 6-(4-methoxy-2,3,6-trimethyl benzoyl)-2-methyl naphthalene carboxylate, (4) 6-(4-methoxy -2,3,6-trimethyl benzoyl)-2-naphthalene carboxylic acid, (5) 6-(4-tert.butyl benzoyl)-2-methyl naphthalene carboxylate, (6) 6-(4-tert.butyl benzoyl)-2-naphthalene carboxylic acid, (7) N-ethyl 6-(4-tert.butyl benzoyl)-2-naphthalene carboxamide, (8) 6-(3-adamantyl-4-methoxy benzoyl)-2-naphthalene carboxylate, (9) 6-(3-adamantyl-4-methoxy benzoyl)-2-naphthalene carboxylic acid,

(10) 6-(4-methoxy benzoyl)-2-methyl naphthalene carboxylate,

(11) 6-(4-cyclohexyl benzoyl)-2-methyl naphthalene.-carboxylate,

(12) 6-(4-cyclohexyl benzoyl)-2-naphthalene carboxylic acid,

(13) 6-(4-methoxy-3-phenyl benzoyl)-2-methyl naphthalene carboxylate,

(14) 6-(4-methoxy-3-phenyl benzoyl)-2-naphthalene carboxylic acid,

(15) 6-(4-phenoxy benzoyl)-2-methyl naphthalene carboxylate,

(16) 6-[(2,4-diisopropyl phenyl) hydroxymethyl]-2-naphthalene carboxylic acid,

(17) 6-[(2,4-diisopropyl phenyl) hydroxymethyl]-2-naphthalene carbinol,

(18) 6-(2,4-diisopropyl benzyl-2naphthalene carboxylic acid,

(19) 4-(2,4-diisopropyl benzoyl) methyl benzoate,

(20) 4-(2,4-diisopropyl benzoyl) benzoic acid,

(21) 4-[(2,4-diisopropyl phenyl) hydroxymethyl]benzoic acid,

(22) 1-(2,4-diisopropyl phenyl)-1-(4-hydroxymethyl phenyl) methanol,

(23) 4-(2,4-diisopropyl benzoyl) benzaldehyde,

(24) 4-(2,4-diisopropyl benzoyl) α-methyl ethyl cinnamate,

(25) 4-(2,4-diisopropyl benzoyl) α-methyl cinnamic acid,

(26) [4-(3-adamantyl-4-methoxy phenyl) hydroxymethyl]methyl benzoate,

(27) 4-[(3-adamantyl-4-methoxyphenyl) hydroxymethyl] benzoic acid,

(28) 4-(3-adamantyl-4-methoxybenzoyl) benzoic acid,

(29) 4-(3-adamantyl-4-hydroxybenzoyl) benzoic acid,

(30) 4-(3-adamantyl-4-hydroxy benzoyl) methyl benzoate,

(31) 4-(3,5-di tert.butyl-4-hydroxy benzoyl) methyl benzoate and

(32) 4-(3,5-di tert.butyl-4-hydroxy benzoyl) benzoic acid.

The present invention also relates to a process for peparing the compounds of formula (I) defined above.

The compounds of formula (II) wherein R' and R" together form an oxo radical and n=0 are obtained in accordance with the following reaction scheme.

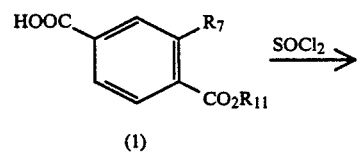

(1)

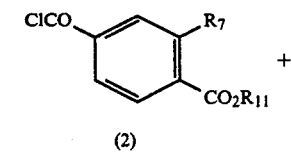

(2)

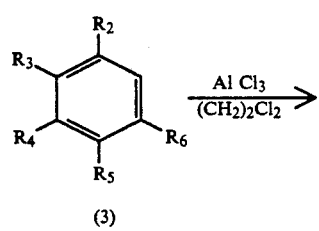

(3)

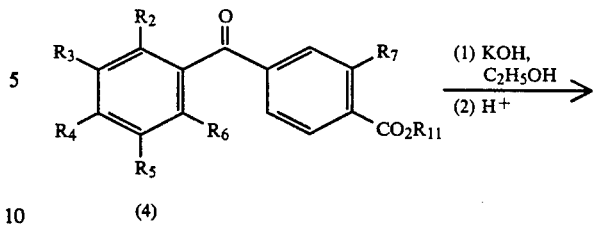

(4)

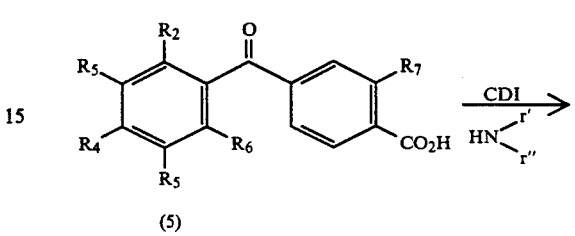

(5)

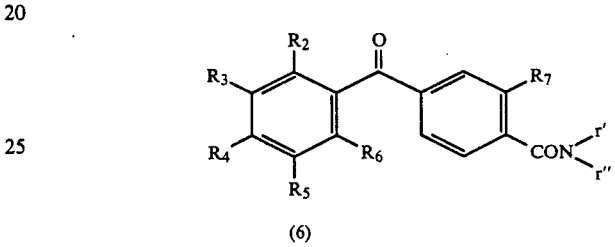

(6)

$R_{11}$=alkyl having 1-20 Carbon atoms.

The starting 4-alkoxycarbonyl benzoic acid is obtained by the oxidation of alkyl 4-formyl benzoate, preferably methyl 4-formyl benzoate which is a commercial product.

The corresponding acid chloride is prepared by the action of thionyl chloride in accordance with conventional methods for preparing acid chlorides.

The condensation reaction of the chloride of 4-alkoxy carbonyl benzoic acid (2) on the benzene derivative (3) is carried out under Friedel-Crafts reaction conditions, i.e. in the presence of anhydrous aluminum chloride in an organic solvent such as 1,2-dichloroethane at a temperature between 0° and 25° C. with stirring.

Starting with the ester (4) there is obtained by saponification the corresponding acid (5) which can then be transformed into the amide of formula (6( by reaction with an amine of the formula

in the presence of N,N'-carbonyldiimidazole (CDI).

For certain meanings of $R_{11}$ of formula (I), in particular when $R_{11}$ represents a monohydroxy or polyhydroxy alkyl radical, it is preferable to prepare the acid (5) starting with the methyl ester (4) ($R_{11}$=—$CH_3$) and then to esterify the resulting acid into the ester of the selected alcohol in accordance with known methods.

When in the compounds of formula (I) n=1, these compounds are obtained in accordance with the following reaction scheme:

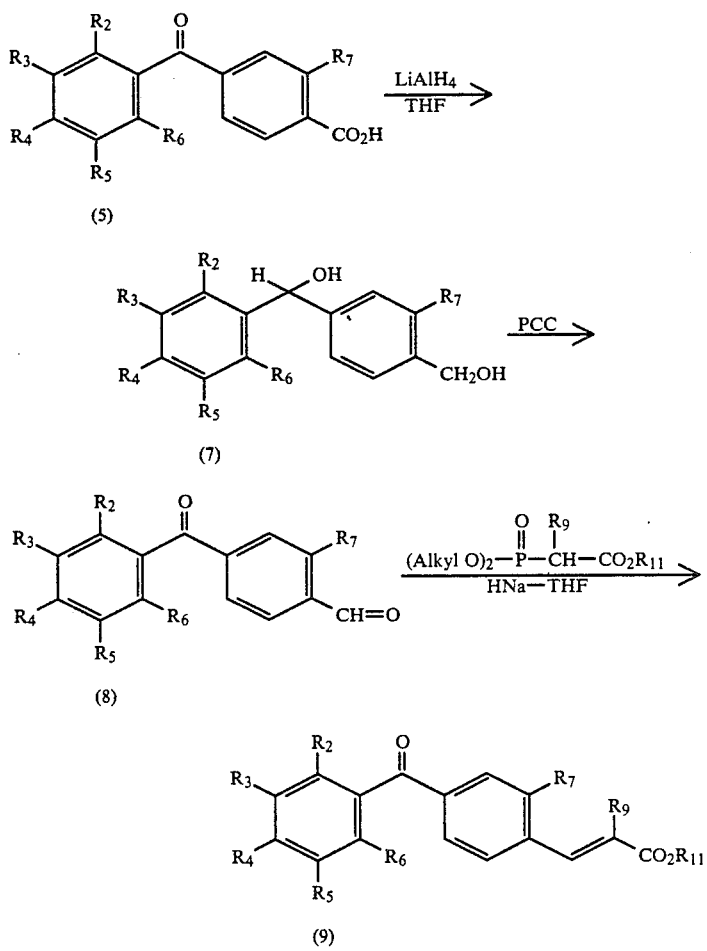

The keto-acid (5) is reduced in the presence of lithium aluminum hydride to the corresponding diol (7) which is then oxidized in the presence of pyridinium chlorochromate (PCC) which leads to the ketoaldehyde (8). The latter, by the Wittig-Horner reaction with an alkyl phosphono acetate, substituted or not, leads, in the presence of sodium hydride in an organic solvent such as THF, to the unsaturated ester of formula (9).

The ester of formula (9) can than be transformed, as before, into the corresponding acid and then into the amide by reaction with an amine of the formula

The compounds of formula (II) wherein R′=H and R″=OH are obtained starting with ketonic derivatives, by reduction with sodium borohydride in THF or methanol.

The compounds of formula (II) wherein R′=R″=H are obtained by the reduction with zinc of the ketonic derivatives, in acetic acid, in the presence of HCl.

These reduction reactions of the carbonyl must however be compatible with the nature of the various substituents ($R_2$ to $R_7$) as well as with the radical $R_1$. It can be desirable to ensure optional protection, however, the reduction of the carbonyl creates no difficulty when $R_1$=—$CO_2H$.

The acyloxy derivatives of the compounds of formula (II) (R′=H and R″=$C_1$-$C_4$ acyloxy) are obtained by reacting an activated form of the acid such as an anhydride or acid chloride with a compound of formula (II) wherein R′=H and R″=OH.

The alkoxy derivatives of the compounds of formula (II) (R′=H and R″=$C_1$-$C_4$ alkoxy) are also obtained starting with the compounds of formula (II) (R′=H and R″=OH) in accordance with known methods.

For the preparation of the acyloxy and alkoxy derivatives it is preferable that the radical $R_1$ is an ester, an acid or an amide function.

The compounds of formula (III) wherein R′ and R″ together form an oxo radical are obtained in acccordance with the following reaction scheme:

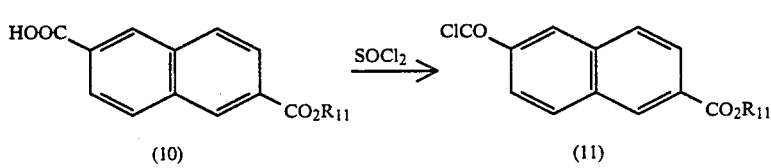

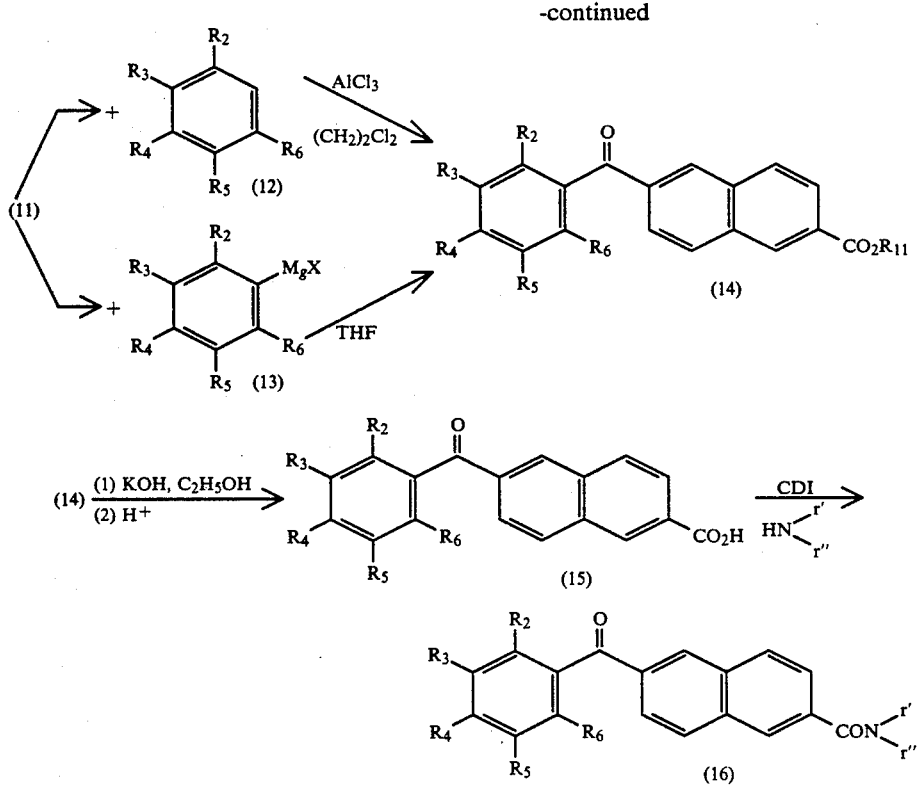

X=Br or Cl and $R_{11}$=$C_1$-$C_{20}$ alkyl

The starting 6-alkoxy carbonyl-2naphthalene carboxylic acid (10) is obtained by the monosaponification reaction of 2,6 alkyl naphthalene dicarboxylate, preferably starting with 2,6 methyl naphthalene dicarboxylate which is a commercial product. The corresponding acid chloride (11) is prepared by reaction with thionyl chloride in accordance with conventional procedures for preparing acid chlorides.

The condensation reaction of the chloride of 6-alkoxy carbonyl-2-naphthalene carboxylic acid (11) can be effected either on the benzene derivative (12), under Friedel-Crafts conditions, or on the magnesium derivative of the halogeno benzene derivative (13).

The Friedel-Crafts reaction conditions are the same as those given above for the preparation of the compounds of formula (4). The preparation of the magnesium derivative of the halogeno benzene derivative (13) is effected in anhydrous THF at reflux and the condensation of the acid chloride is carried out at a temperature of about 0° C. in the same solvent.

In accordance with the same methods as those described above for the compounds of formula (II) the other compounds of formula (III) can be prepared, i.e. compounds of formulas (15) and (16) as well as compounds of formula (III) wherein R' and R", taken together, are other than an oxo radical.

The present invention further relates to a medicine comprising the compounds of formula (I) as defined above.

These compounds exhibit excellent activity in the inhibition test of ornithine decarboxylase in nude rats, after induction, by "tape stripping", M. Bouclier, et al, Dermatologica 169, No. 4 (1984). This test is recognized as a measure of an antiproliferative activity.

These compounds are particularly appropriate for treating dermatologic ailments linked to a keratinization disorder (differentiation-proliferation) as well as dematologic diseases, or others, having an inflammatory and/or immunoallergic component, principally:

acne vulgaris, comedons or polymorphs, solar senile acne and medicinal or professional acne, extensive and/or severe forms of psoriasis and other keratinization disorders, and principally ichtysoses and ichtysosis like conditions, Darier malady, palmo-plantar keratodermies, leucophasies and leucophasie-like states, lichen plan, all malignant or benign dermatologic proliferations, severe or extensive.

They are also active in the treatment of tumors, of rheumatoid psoriasis, cutaneous or respiratory atophies as well as in certain opthalmologic problems relating to corneopathies.

Thus, the present invention also relates to medicinal compositions containing at least one compound of formula (I), such as defined above, or one of its salts or one of its optical or geometric isomers.

The present invention thus relates to a new medicinal composition, intended principally for the treatment of the above-mentioned disorders, an effective amount of at least one compound of formula (I) and/or one of its salts and/or one of its optical or 9eometric isomers.

The compounds accordin9 to the present invention are generally administered at a daily dosage of about 2µg/kg to 2mg/kg of body weight.

As the vehicle or carrier for these compositions any conventional vehicle can be employed, the active component being found either in the dissolved state, or in the dispersed state, in said vehicle.

The administration of the compounds of the present invention can be effected enterally, parenterally, topically or ocularly.

When administered enterally, the medicines can be provided in the form of tablets, gelules, lozenges, syrups, suspensions, solutions, powders, granules or emulsions.

When administered parenterally, the medicinal compositions can be provided in the form of solutions or suspensions for perfusion or injection.

When administered topically, the pharmaceutical compositions, based on the compounds according to the present invention, can be provided in the form of ointments, tinctures, creams, salves, powders, pads, impregnated tampons, solutions, lotions, gels, sprays or suspensions.

These compositions for topical administration can be provided under anhydrous form or in aqueous form according to clinical indications.

When administered ocularly, the is provided principally in the form of an eyewash.

The compositions for topical or ocular administration contain preferably from 0.0005 to about 5 percent by weight of at least one compound of formula (I) such as defined above relative to the total weight of the composition.

The compounds of formula (I), according to the present invention, are also useful in the cosmetic field, in particular in body and hair hygiene compositions and principally for the treatment of skin having acne tendencies, to improve the growth of hair, to combat hair loss, to combat against an only appearance of the skin or hair, in the prevention or treatment of the harmful effects of the sun or in the treatment of physiologically dry skin.

The present invention thus relates to a cosmetic composition containing, in a cosmetically acceptable vehicle, an effective amount of at least one compound of formula (I) or one of its salts and/or one of its isomers, this composition being provided principally in the form of a lotion, gel, cream, soap or shampoo.

The concentration of the compound of formula (I) in these cosmetic compositions is between 0.0005 and 2 percent by weight and, preferably, between 0.01 and 1 percent by weight based on the total weight of the composition.

The medicinal and cosmetic compositions according to the present invention can contain inert or even pharmacodynamic or cosmetically active additives and, principally: hydrating agents such as thiamorpholinone and its derivatives or urea; antiseborrheic or anti-acne agents such as S-carboxymethylcysteine, 5-benzylcysteamine, their salts and their derivatives, tioxolone or benzoyl peroxide; antibiotics such as erythromycin and its esters, neomycin, tetracyclines and 4,5-polymethylene-3-isothiazolones; agents promoting the growth of hair such as "Minoxidil" (2,4-diamino-6-piperidino-3-pyrimidine oxide) and its derivatives, Diazoxide (7-chloro-3-methyl-1,2,4-benzothiadiazine-1,1-dioxide) and Phenytoin (5,5-diphenyl-2,4imidazolidine dione); steroidal and non-steriodal anti-inflammatory agents; carotenoids and, principally, $\beta$-carotene; anti-psoriasic agents such as anthralin and its derivatives and 5,8,11,14-eicosatetraynoic and 5,8,11-eicosatriynoic acids, and their esters and amides.

The compositions according to the present invention can also include flavor improving agents, preservatives, stabilizers, humidity regulating agents, pH regulating agents, osmotic pressure modifying agents, emulsifiers, UV-A and UV-B filters, anti-oxidants such as $\alpha$-tocopherol, butylhydroxyanisole or butylhydroxy toluene.

The following non-limiting examples illustrate the preparation of the active compounds of formula (I) according to the present invention as well as compositions containing the compounds.

EXAMPLES OF PREPARATION

Example 1

Preparation of 6-(2,4-diisopropyl benzoyl)-2-methyl naphthalene carboxylate

Compound of formula V wherein $R'_{10}$'$OCH_3$, $R'_2=R''_4=isoC_3H_7$.

To a suspension of 1.62 g (10 mmoles) of m-diisopropylbenzene and 2.49 g (10 mmoles) of 6-methoxy carbonyl-2-naphthalene carboxylic acid chloride in 80cm$^3$ of anhydrous 1,2-dichloroethane, there are added, by portions, 1.87 g (14 mmoles) of anhydrous aluminum chloride. The mixture is stirred for 4 hours at ambient temperature and then poured into 100 cm$^3$ of acidulated ice water. The organic phase is decanted. The aqueous phase is extracted twice with 70 cm$^3$ of dichloroethane. The dichloroethane phases are combined, washed with sodium bicarbonate and then with water, dried on sodium sulfate and then concentrated. The resulting solid is purified by silica gel chromatography in a 60/40 toluene/dichloromethane mixture followed by a repasting in isopropyl ether. After filtering and drying 1.2 g of 6-(2,4-diisopropylbenzoyl)-2-methyl naphthalene carboxylate in the form of a white powder whose melting point is 71°–73° C. are obtained.

The NMR$^1$H spectrum 60 MHz conforms to the expected structure.

Elemental analysis: $C_{25}H_{25}O_3$.

| Elemental analysis: $C_{25}H_{25}O_3$ | | |
|---|---|---|
| | C % | H % | O % |
| Calculated: | 80.40 | 6.75 | 12.85 |
| Found: | 80.16 | 7.00 | 13.13 |

Example 2

Preparation of 6-(2,4-diisopropylbenzoyl)-2-naphthalene carboxylic acid

Compound of formula V wherein $R'_{10}=OH$, $R'_2=R''_4=isoC_3H_7$.

A suspension of 0.9g (2.4mmoles) of 6-(2,4-diisopropyl benzoyl)-2-methyl naphthalene carboxylate obtained in Example 1 is stirred for 2 hours in a mixture of 15 cm$^3$ of alcohol and 15 cm$^3$ of 6N aqueous potash heated to reflux. After the addition of 50 cm$^3$ of water, the alcohol is removed by evaporation under a vacuum. The resulting aqueous phase is diluted to 200cm$^3$, cooled to between 0 and 5° C. and then acidified with 15 cm$^3$ of 12N HCl. The resulting precipitate is filtered, washed with water and dried at 80° C. on potash.

After recystallization in isopropylether, 0.5g of white crystals of 6-(2,4-diisopropyl benzoyl)-2-naphthalene carboxylic acid whose melting point is 187°–189° C. is obtained.

The NMR$^1$H spectrum 250 MHz conforms to the expected structure.

Elemental Analysis: $C_{24}H_{24}O_3$.

| Elemental Analysis: C$_{24}$H$_{24}$O$_3$ | | | |
|---|---|---|---|
| | C % | H % | O % |
| Calculated: | 79.97 | 6.71 | 13.32 |
| Found: | 39.94 | 6.72 | 13.25 |

Example 3

Preparation of 6-(4-methoxy-2,3,6-trimethyl benzoyl)-2-methyl naphthalene carboxylate Compound of formula VI wherein R'$_{10}$=—OCH$_3$, R"$_2$=R'$_3$=R'$_6$=CH$_3$, R'$_{12}$=CH$_3$.

To a suspension of 1.5g (10 mmoles) of 2,3,5-trimethyl anisole and 2.5g (10 mmoles) of 6-methoxycarbonyl-2-naphthalene carboxylic acid chloride in 80 cm$^3$ of anhydrous 1,2-dichloroethane, there are added, by portions, 1.87 g (14 mmoles) of anhydrous aluminum chloride. The mixture is stirred for three hours at ambient temperature and then poured into 100 cm$^3$ of acidulated ice water. The organic phase is decanted. The aqueous phase is then extracted once with 100 cm$^3$ of dichloroethane. The dichloroethane phases are combined, washed with sodium bicarbonate and then with water, dried on sodium sulfate and concentrated. The resulting solid is purified by silica gel chromotography in a 60/40 toluene/dichloromethane mixture. After evaporation.and drying, 1.2 g of 6-(4-methoxy-2,3,6-trimethyl benzoyl)-2-methyl naphthalene carboxylate in the form of a yellow powder whose melting point is 144°-145° C. are obtained.

The NMR$^1$H spectrum 60 MHz conforms to the expected structure.

Elemental Analysis: C$_{23}$H$_{22}$O$_4$.

| Elemental Analysis: C$_{23}$H$_{22}$O$_4$ | | | |
|---|---|---|---|
| | C % | H % | O % |
| Calculated: | 76.22 | 6.12 | 17.66 |
| Found: | 76.30 | 6.09 | 17.50 |

Example 4

Preparation of 6-(4-methoxy-2,3,6-trimethyl benzoyl)-2-naphthalene carboxylic acid.

Compound of formula VI wherein R'=OH, R"$_2$=R'$_3$=R'$_6$=CH$_3$, R'$_{12}$=CH$_3$.

A suspension of 0.98 g (2.7 mmoles) of 6(4-methoxy-2,3,6-trimethyl benzoyl)-2-methyl naphthalene carboxylate obtained in Example 3 is stirred for 2 hours in a mixture of 20 cm$^3$ of alcohol and 20 cm$^3$ of 6N aqueous potash heated to reflux. After the addition of 60 cm$^3$ of water, the alcohol is removed by evaporation under a vacuum. The resulting aqueous phase is diluted to 300 cm$^3$, cooled to between 0° and 5° C. and then acidified with 20 cm$^3$ of 12N HCl. The resulting precipitate is filtered, washed with water and dried at 80° C. on potash.

After recystallization, at first in a cyclohexane/ethylacetate mixture and then in a hexane/acetone mixture, 0.71 g of white crystals of 6-(4-methoxy-2,3,6-trimethyl benzoyl)-2-naphthalene carboxylic acid whose melting point is 260° C. is obtained.

The NMR$^1$H spectrum 250 MHz conforms to the expected structure.

Elemental Analysis: C$_{22}$H$_{20}$O$_4$.

| Elemental Analysis: C$_{22}$H$_{20}$O$_4$ | | | |
|---|---|---|---|
| | C % | H % | O % |
| Calculated: | 75.84 | 5.79 | 18.37 |
| Found: | 75.64 | 5.87 | 18.50 |

Example 5

Preparation of 6-(4-tert.butyl benzoyl)-2-methyl naphthalene carboxylate.

Compound of formula V wherein R'$_{10}$=OCH$_3$, R'$_2$=H, R"$_4$=tert.C$_4$H$_9$.

To a suspension of 1.16 g (12 mmoles) of tert.butyl benzene and 3 g (12 mmoles) of 6-methoxycarbonyl-2-naphthalene carboxylic acid chloride in 80 cm$^3$ of anhydrous 1,2-dichloroethane, there are added, by portions, 3.2 g (24 mmoles) of anhydrous aluminum chloride. The mixture is stirred for 5 hours at ambient temperature and then poured into 100 cm$^3$ of acidulated ice water. The organic phase is decanted and the aqueous phase once again extracted with 100 cm$^3$ of dichloroethane. The dichloroethane phases are combined, washed with sodium bicarbonate, dried on sodium sulfate and then concentrated. The resulting crude solid is recrystallized twice in methanol and then once in isopropanol. After drying, 1.62 g of white crystals of 6-(4-tert.butyl benzoyl)-2-methyl naphthalene carboxylate whose melting point is 133.5°-134.5° C. are obtained.

The NMR$^1$H spectrum 60 MHz conforms to the expected structure.

Elemental Analysis: C$_{23}$H$_{22}$O$_3$.

| Elemental Analysis: C$_{23}$H$_{22}$O$_3$ | | | |
|---|---|---|---|
| | C % | H % | O % |
| Calculated: | 79.74 | 6.40 | 13.86 |
| Found: | 79.88 | 6.50 | 13.53 |

Example 6

Preparation of 6-(4-tert.butyl benzoyl)-2-naphthalene carboxylic acid.

Compound of formula V wherein R'$_{10}$=OH, R'$_2$=H, R"$_4$=tert.C$_4$H$_9$.

A suspension of 1.25 g (3.6 mmoles) of 6(4-tert.butyl benzoyl)-2-methyl naphthalene carboxylate obtained in Example 5 is stirred for 2 hours in a mixture of 25 cm$^3$ of alcohol and 25 cm$^3$ of 6N aqueous potash heated at reflux. After addition of 100 cm$^3$ of water, the alcohol is removed by evaporation under a vacuum. The resulting aqueous phase is diluted to 250cm$^3$, cooled to between 0° and 5° C. and then acidified with 20 cm$^3$ of 12N HCl. The resulting precipitate is filtered, washed with water and dried at 80° C. on potash.

After recrystallization in isopropylether, 0.84 g of white crystals of 6-(4-tert.butyl benzoyl)-2-naphthalene carboxylic acid whose melting point is 233°-234° is obtained.

The NMR$^1$H spectrum 250 MHz conforms to the expected structure.

Elemental Analysis: C$_{22}$H$_{20}$O$_3$.

| Elemental Analysis: C$_{22}$H$_{20}$O$_3$ | | | |
|---|---|---|---|
| | C % | H % | O % |
| Calculated: | 79.49 | 6.06 | 14.44% |

-continued

Elemental Analysis: $C_{22}H_{20}O_3$

|  | C % | H % | O % |
|---|---|---|---|
| Found | 79.54 | 6.07 | 14.36 |

Example 7

Preparation of N-ethyl 6-(4-tert.butyl benzoyl)-2-naphthalene carboxamide

Compound of formula V wherein $R'_{10}$=—$NHC_2H_5$, $R'_2$=H, $R''_4$=tert.$C_4H_9$ A suspension of 250mg (0.75 mmole) of 6-(4-tert.butyl benzoyl)-2-naphthalene carboxylic acid obtained in Example 6 and 150 mg (0.92 mmole) of N,N'-carbonyldiimidazole in 8 cm³ of anhydrous dichloromethane is stirred for 1 hour at ambient temperature. 0.06 cm³ (0.88 mmole) of anhydrous ethylamine is added to the resulting solution. After stirring for 1 hour, the reaction mixture is diluted with 20 cm³ of dichloromethane, washed successively with 10 cm³ of water, 10 cm³ of normal NaOH, 10 cm³ of water, 10 cm³ of normal HCl and finally with 10 cm³ of water. The dichloromethane phase is dried on sodium sulfate and then evaporated to dryness. The crude amide is dried under a vacuum at 60° C., then recrystallized in isopropyl ether. 190mg of white crystals of N-ethyl 6-(4-tert.butyl benzoyl)-2-naphthalene carboxamide whose melting The NMR¹H spectrum 250 MHz conforms to the expected structure. point is 139° C. are obtained.

The NMR¹H spectrum 250 MHz conforms to the expected structure.

Elemental Analysis: $C_{24}H_{25}NO_2$.

| Elemental Analysis: $C_{24}H_{25}NO_2$ | | | | |
|---|---|---|---|---|
|  | C % | H % | N % | O % |
| Calculated: | 80.19 | 7.01 | 3.90 | 8.90 |
| Found: | 79.98 | 7.00 | 4.03 | 9.11 |

Example 8

- Preparation of 6-(3-adamantyl-4-methoxy benzoyl)-2-methyl naphthalene carboxylate Compound of formula VI wherein $R'_{10}$=$OCH_3$, $R''_2$ $R'_6$ $R'_3$=adamantyl, $R'_{12}$=$CH_3$ A solution of 6.6 g (0.02 mole) of 2-adamantyl-4-bromo anisole in 75 cm³ of anhydrous tetrahydrofuran is added to 500mg (0.02 mole) of magnesium covered with tetrahydrofuran and brought to reflux until the complete disappearance of the magnesium. The reaction mixture is then cooled to 0° C. at which point it is added to a solution of 2.5 g of (0.01 mole) of 6-methoxycarbonyl-2-naphthalene carboxylic acid chloride in anhydrous THF. The mixture is maintained for 1 hour at ambient temperature, then poured into an aqueous solution of ammonium chloride. The expected product is extracted with ether, then dried on magnesium sulfate and concentrated under reduced pressure. The 6-(3-adamantyl-4 methoxy benzoyl)-2-methyl naphthalene carboxylate is purified by silica gel chromatography (eluant: hexane/ethyl acetate), then crystallized in methanol.

1.2 g of a white powder whose melting point is 130-132° C. are obtained.

The NMR¹H spectrum 250MHz conforms to the expected structure.

Example 9

- Preparation of 6-(3-adamantyl-4-methoxy benzoyl)-2-naphthalene carboxylic acid Compound of formula VI wherein $R'_{10}$=OH, $R''_2$=$R'_6$=H, $R'_3$=1-adamantyl, $R'_{12}$=—$CH_3$ A suspension of 1g of 6-(3-adamantyl-4-methoxy benzoyl)-2-methyl naphthalene carboxylate obtained in Example 8 is stirred for 1 hour in a mixture of 50 cm³ of ethanol and 50 cm³ of 6N aqueous potash at a temperature between 50 and 60° C. After having added 100 cm³ of water, the ethanol is removed by evaporation under a vacuum. The aqueous phase is acidified to pH 1 by the addition of HCl then extracted with 2×100 cm³ of ethyl acetate. The organic phase is dried and concentrated under reduced pressure. The 6-(3-adamantyl-4-methoxy benzoyl)-2-naphthalene carboxylic acid crystallizes in methanol. After evaporation, a slightly pink powder whose melting point is 270-272° C., is obtained.

Elemental Analysis: $C_{29}H_{28}O_4$.

| Elemental Analysis: $C_{29}H_{28}O_4$ | | | |
|---|---|---|---|
|  | C % | H % | O % |
| Calculated: | 79.06 | 6.40 | 14.52 |
| Found: | 78.58 | 6.43 | 14.64 |

Example 10

Preparation of 6-(4-methoxy benzoyl)-2-methyl naphthalene carboxylate

Compound of formula VI wherein $R'_{10}$=$OCH_3$, $R''_2$=$R'_3$=$R'_6$=H, $R'_{12}$=$CH_3$.

To a solution of 4.5 g (0.04 mole) of anisole and 10 g (0.04 mole) of 6-methoxy carbonyl-2naphthalene carboxylic acid chloride in about 80 cm³ of anhydrous dichloroethane, there are added, in small portions, 8.05 g (0.06 mole of anhydrous aluminum chloride. The mixture is left overnight at ambient temperature, then poured into 100 cm³ of ice water. The organic phase is decanted. The aqueous phase is extracted with 300 cm³ of dichloromethane. The organic phases are combined, washed with sodium bicarbonate, dried on magnesium sulfate then concentrated under reduced pressure. The expected product is purified by recrystallization in acetonitrile followed by a recrystallization in methylethylketone. 2.5 g of a white powder whose melting point is 170-171° C. are obtained.

Elemental Analysis: $C_{20}H_{16}O_4$.

| Elemental Analysis: $C_{20}H_{16}O_4$ | | | |
|---|---|---|---|
|  | C % | H % | O % |
| Calculated: | 74.98 | 5.03 | 19.97 |
| Found: | 75.05 | 4.95 | 19.94 |

Example 11

Preparation of 6-(4-cyclohexyl benzoyl)-2-methyl naphthalene carboxylate

Compound of formula V wherein $R_{10}$=$OCH_3$, $R_2$=H, $R''_4$=cyclohexyl

To a suspension of 2.08 g (13 mmoles) of phenylcyclohexane and 3.23 g (13 mmoles) of 6-methoxycarbonyl-2-naphthalene carboxylic acid chloride in 80 cm³ of anhydrous 1,2-dichloroethane, there are added, in portions, 3.33 g (25 mmoles) of anhydrous aluminum chloride. The mixture is stirred for 6 hours at ambient temperature, then poured into 150 cm³ of acidulated ice water. The organic phase is decanted. The aqueous phase is extracted twice with 60 cm³ of dichloroethane. The dichloroethane dried on sodium sulfate, then concentrated under reduced pressure. The crude product is recrystallized twice in methanol, then in isopropanol. After drying, 2.4 g of white crystals of 6-(4-cyclohexyl benzoyl)-2-methyl naphthalene carboxylate whose melting point is 130° C. are obtained.

The NMR¹H spectrum 60 MHz conforms to the expected structure.

Elemental Analysis: $C_{25}H_{24}O_3$.

| Elemental Analysis: $C_{25}H_{24}O_3$ | | | |
|---|---|---|---|
| | C % | H % | O % |
| Calculated: | 80.62 | 6.50 | 12.89 |
| Found: | 80.12 | 6.58 | 13.28 |

Example 12

Preparation of 6-(4-cyclohexyl benzoyl)-2-naphthalene carboxylic acid

Compound of formula V wherein $R'_{10}$=OH, $R'_2$=H $R''_4$=cyclohexyl

A suspension of 1.2 g (3.2 mmoles) of 6-(4cyclohexyl benzoyl)-2-methyl naphthalene carboxylate, obtained in Example 11, is stirred for 3 hours in a mixture of 25 cm³ of alcohol and 25 cm³ of 6N aqueous potash heated to reflux. After the addition of 150 cm³ of water, the alcohol is removed by evaporation under a vacuum. The resulting aqueous phase is diluted to 400cm³, cooled to between 0 and 5° C., then acidified with 20 cm³ of 12N HCl. The resulting precipitate is filtered, washed with water and dried under a vacuum at 80° C. After recrystallization in isopropyl alcohol, 0.95 g of pinkish white crystals of 6-(4-cyclohexyl benzoyl)-2-naphthalene carboxylic acid whose melting point is 241°-242° C. is obtained.

The NMR¹H spectrum 250 MHz conforms to the expected structure.

Elemental Analysis: $C_{24}H_{22}O_3$.

| Elemental Analysis: $C_{24}H_{22}O_3$ | | | |
|---|---|---|---|
| | C % | H % | O % |
| Calculated: | 80.42 | 6.19 | 13.39 |
| Found: | 80.36 | 6.19 | 13.23 |

Example 13

Preparation of 6 (4-methoxy-3-phenyl benzoyl)-2-methyl naphthalene carboxylate

Compound of formula VI wherein $R'_{10}$=OCH₃, $R''_2$=$R'_6$=H, $R'_3$=$C_6H_5$, $R'_{12}$=CH₃.

To a suspension of 2.4 g (13 mmoles) of 2-methoxybiphenyl and 3.23 g (13 mmoles) of 6-methoxycarbonyl-2-naphthalene carboxylic acid chloride in 80 cm³ of anhydrous 1,2-dichloroethane, there are added, by portions, 3.33 g (25 mmoles) of anhydrous aluminum chloride. The mixture is stirred for 4 hours at ambient temperature, then poured into 150 cm³ of acidulated ice water. The organic phase is decanted. The aqueous phase is extracted twice with 60 cm³ of dichloroethane. The dichloroethane phases are combined, washed with sodium bicarbonate, dried on sodium sulfate then concentrated under reduced pressure. The resulting solid is taken up in 200 cm³ of methanol, filtered and recrystallized twice in methanol, then acetonitrile. After drying, 2 g of white crystals of 6-(4-methoxy-3-phenyl benzoyl)-2-methyl naphthalene carboxylate whose melting point is 160°-162° are obtained.

The NMR¹H spectrum 60 MHz conforms to the expected structure.

Elemental Analysis: $C_{26}H_{20}O_4$.

| Elemental Analysis: $C_{26}H_{20}O_4$ | | | |
|---|---|---|---|
| | C % | H % | O % |
| Calculated: | 78.77 | 5.09 | 16.14 |
| Found: | 78.79 | 5.08 | 15.98 |

Example 14

Preparation of 6-(4-methoxy-3-phenyl benzoyl-2-naphthalene carboxylic acid

Compound of formula VI wherein $R'_{10}$=OH, $R''_2$=$R'_6$=H, $R'_3$=$C_6H_5$, $R'_{12}$=CH₃.

A suspension of 1.3 g (3.28 mmoles) of 6-(4-methoxy-3-phenyl benzoyl)-2-methyl naphthalene carboxylate, obtained in Example 13, is stirred for 3 hours in a mixture of 30 cm³ of alcohol and 30 cm³ of 6N aqueous potash heated at reflux. After the addition of 200 cm³ of water, the alcohol is removed by evaporation under a vacuum. The resulting aqueous phase is diluted with 500 cm³ of water, cooled to between 0 and 5° C., then acidified with 25 cm³ of 12N HCl. The resulting precipitate is filtered, washed with water and dried under a vacuum at 80° C. The crude product is rapidly purified by silica 60 gel chromatography, eluted initially with dichloromethane then with a dichloromethane/isopropanol mixture. After evaporation under a vacuum and recrystallization in an acetonitrile/acetic acid mixture, 0.6 g of white crystals of 6-(4-methoxy-3-phenyl benzoyl)-2-naphthalene carboxylic acid having a melting point of 221-223° C. is obtained.

The NMR¹H spectrum 250 MHz conforms to the expected structure.

Elemental Analysis: $C_{25}H_{18}O_4$.

| Elemental Analysis: $C_{25}H_{18}O_4$ | | | |
|---|---|---|---|
| | C % | H % | O % |
| Calculated: | 78.52 | 4.74 | 16.74 |
| Found: | 78.63 | 4.83 | 16.55 |

Example 15

Preparation of 6-(4-phenoxy benzoyl)-2-methyl naphthalene carboxylate

Compound of formula VI wherein $R'_{10}$=OCH₃, $R''_2$=$R'_3$=$R'_6$='H, $R'_{12}$=$C_6H_5$.

To a suspension of 2.21 g (13 mmoles) of diphenyl ether and 3.23 g (13 mmoles) of 6-methoxycarbonyl-2-naphthalene carboxylic acid chloride in 80 cm³ of anhydrous 1,2-dichloroethane, there are added, by portions, 3.33 g (25 mmoles) of anhydrous aluminum chloride. The mixture is stirred for 5 hours at ambient temperature and then poured into 150 cm³ of acidulated ice water. The organic phase is decanted and the aqueous phase is extracted twice with 80 cm³ of dichloroethane. The dichloroethane phases are combined, washed with sodium bicarbonate, dried on sodium sulfate, then concentrated under reduced pressure. The resulting solid is purified by washing with boiling methanol, then recrystallized in isopropanol. After drying, 3.2 g of white crystals of 6-(4-phenoxybenzoyl)-2-methyl naphthalene carboxylate whose melting point is 173° C. are obtained.

The NMR$^1$H spectrum 60MHz conforms to the expected structure

Elemental Analysis: $C_{25}H_{18}O_4$.

| Elemental Analysis: $C_{25}H_{18}O_4$ | | | |
|---|---|---|---|
| | C % | H % | O % |
| Calculated: | 78.52 | 4.74 | 16.74 |
| Found | 78.55 | 4.83 | 16.64 |

Example 16

Preparation of 6-[(2,4-diisopropyl phenyl) hydroxmethyl]-2-napthalene carboxylic acid Compound of formula III wherein R'=H, R''=OH, $R_2=R_4$=iso $C_3H_7$, $R_3=R_5=R_6$=H, $R_1$=—$CO_2H$ To a solution of 0.54 g (1.5 mmoles) of 6-(2,4-diisopropyl benzoyl)-2-naphthalene carboxylic acid, obtained in Example 2, in 15 cm$^3$ of anhydrous tetrahydrofuran, cooled to 0° C., there are added 170mg (4.5 mmoles) of sodium borohydride. The reaction mixture is stirred for 1 hour while letting it return to ambient temperature. It is then heated for about 30 minutes up to the reflux. The reduction is then complete.

The reaction mixture is then cooled to 0° C., acidified by the slow addition of 0.1N HCl and extracted with ethyl ether.

The ether phase is washed with water, dried on sodium sulfate and evaporated to dryness. The resulting crude product is recrystallized in hexane containing a small amount of acetone. After drying at 70° C., 0.4 g of white crystals of 6-[(2,4-diisopropyl phenyl) hydroxymethyl]-2-naphthalene carboxylic acid whose melting point is 225° C. is obtained.

The NMR$^1$H spectrum 250 MHz conforms to the expected structure.

Elemental Analysis: $C_{24}H_{26}O_3$.

| Elemental Analysis: $C_{24}H_{26}O_3$ | | | |
|---|---|---|---|
| | C % | H % | O % |
| Calculated | 79.53 | 7.23 | 13.24 |
| Found: | 79.16 | 7.23 | 13.44 |

Example 17

Preparation of 6-[(2,4-diisopropyl phenyl) hydroxymethyl]-2-naphthalene carbinol Compound of formula III wherein R'=H, R''=OH, $R_2=R_4$=iso $C_3$ $H_7$, $R_3=R_5=R_6$=H, $R_1=CH_2OH$.

To a suspension of 230 mg (6 mmoles) of lithium aluminum hydride in 5 cm$^3$ of anhydrous tetrahydrofuran, cooled to -10° C., there is added a solution of 0.72 g (2 mmoles) of 6-(2,4-diisopropyl benzoyl)-2-napthalene carboxylic acid, obtained in Example 2, in 10 cm$^3$ of anhydrous tetrahydrofuran.

After stirring for 1 hour while letting the reaction mixture return to ambient temperature, the reaction mixture is cooled to 0° C., acidified by the slow addition of 0.1N HCl and extracted with a ethyl ether.

The ether phase is washed with water, dried on sodium sulfate and evaporated to dryness. The crude product is purified by rapid chromatography on silica 60 in a 30/40/30 eluant mixture of toluene/dichloromethane/ethylacetate, respectively, followd by recrystallization in a hexane/acetone mixture.

After drying under a vacuum at 70° C., 0.52 g of white needles of 6-[(2,4-diisopropyl phenyl) hydroxmethyl]-2-napthalene carbinol whose melting point is 136° C. is obtained.

The NMR$^1$H spectrum 250MHz conforms to the expected structure.

Elemental Analysis: $C_{24}H_{28}O_2$.

| Elemental Analysis: $C_{24}H_{28}O_2$ | | | |
|---|---|---|---|
| | C % | H % | O % |
| Calculated | 82.72 | 8.10 | 9.18 |
| Found: | 82.54 | 8.07 | 9.48 |

Example 18

Preparation of 6-(2,4-diisopropyl benzyl)-2-napthalene carboxylic acid

Compound of formula III wherein R'=R''=$R_3=R_5=R_6$=H, $R_2=R_4$=iso $C_3H_7$ and $R_1$=-$CO_2H$.

To a suspension of 1.3 g (20 mmoles) of powdered zinc in 20 cm$^3$ of glacial acetic acid, there is added 0.72 g (2 mmoles) of 6-(2,4-diisopropyl benzoyl)-2-napthalene carboxylic acid obtained in Example 2. The reaction mixture is heated for 1 hour at reflux. 2 cm$^3$ of 12N HCl are slowly added and the reaction mixture is maintained at reflux for 30 minutes.

After cooling to ambient temperature and adding 20 cm$^3$ of 12N HCl, the reaction mixture is diluted with 100 cm$^3$ of water and extracted with dichloromethane. The organic phase is washed with water, dried on sodium sulfate and concentrated under reduced pressure. The resulting crude product is purified by chromatography on silica 60 gel in a 30/40/30 eluant mixture of toluene/dichloromethane/ethyl acetate, respectively, followed by recrystallization in hexane containing a trace of acetone.

After drying under a vacuuum at 60° C., 0.4 g of white crystals of 6-(2,4-diisopropyl benzyl)-2-napthalene carboxylic acid whose melting point is 183°-185° C. is obtained.

The NMR$^1$H spectrum 250 MHz conforms to the exptected structure.

Elemental Analysis: $C_{24}H_{26}O_2$.

| Elemental Analysis: $C_{24}H_{26}O_2$ | | | |
|---|---|---|---|
| | C % | H % | O % |
| Calculated: | 83.20 | 7.56 | 9.24 |
| Found: | 83.08 | 7.49 | 9.41 |

Example 19

Preparation of 4-(2,4-diisopropyl benzoyl) methyl benzoate

Compound of formula IV wherein $R'_2=R'_4$=iso $C_3$ $H_7$, R' and R''=oxo, $R'_3=R'_5$=H, and R'$_1$=-$CO_2CH_3$.

To a solution, stirred at ambient temperature, of 1.20 cm³ of 1,3-diisopropyl benzene (0.011 mole) and 2 g (0.01 mole) of 4-methoxy carbonyl benzoic acid chloride in 50 cm³ of anhydrous 1,2-dichlorethane there are added, in small portions, 2.40 g of powdered anhydrous aluminum chloride in a manner to maintain the temperature lower than 35° C.

Stirring is continued for 1 hour up to the complete disappearance of the initial reactant. The reaction mixture is poured into 100 cm³ of ice water and extracted with dichloromethane. The organic phase is washed with an aqueous solution of sodium dihydrogencarbonate, then with water, dried on magnesium sulfate and concentrated under reduced pressure.

An oil is recovered which crystallizes in hexane. 2.7 g of 4-(2,4-diisopropyl benzoyl) methyl benzoate melting at 64°-65° C. are obtained.

The NMR¹H spectrum 80 MHz conforms to the expected structure.

Elemental Analysis: $C_{21}H_{24}O_3$.

|  | C % | H % | O % |
|---|---|---|---|
| Calculated: | 77.75 | 7.46 | 14.79 |
| Found: | 77.55 | 7.46 | 14.87 |

Example 20

Preparation of 4-(2,4-diisopropyl benzoyl) benzoic acid

Compound of formula IV wherein
$R'_2 = R'_4 = $ iso $C_3H_7$, R' and R" = oxo, $R'_3 = R'_5 = H$ and $R'_1 = -CO_2H$.

To a solution of 2.7 g of 4-(2,4diisopropyl benzoyl) methyl benzoate, obtained in Example 19, in 200 cm³ of absolute alcohol there are added 75 cm³ of a 6N aqueous solution of potash. The reaction mixture is heated to 40° C. for about 1 hour until the total disappearance of the initial reactant, then the alcohol is evaporated under reduced pressure. The aqueous phase is diluted with 300 cm³ of water, cooled to 0° C. and acidified with concentrated HCl.

The resulting product is filtered and recrystallized in a toluene/hexane mixture 1.3 of a white powder melting at 181°-182° C. are recovered.

The NMR¹H spectrum 80 MHz conforms to the expected structure.

Elemental Analysis: $C_{20}H_{22}O_3$.

|  | C % | H % | O % |
|---|---|---|---|
| Calculated: | 77.39 | 7.15 | 15.46 |
| Found: | 77.19 | 7.15 | 15.56 |

Example 21

Preparation of 1-(2,4-diisopropyl phenyl)-1-(4-hydroxymethyl phenyl) methanol

Compound of formula IV where
R' = $R'_4$ = iso $C_3H_7$, R' = H, R" = OH, $R'_3 = R'_5 = H$ and R'l = —$CH_2OH$ To a suspension of 3.5 g of lithium aluminum hydride in 200 cm³ of anhydrous tetrahydrofuran maintained at 0° C., there is slowly added a solution of 10 g of 4-(2,4-diisopropyl benzoyl) methyl benzoate, obtained in Example 19, in 50 cm³ of tetrahydrofuran. At the end of the addition, stirring of the reaction mixture is maintained, at ambient temperature, until the complete disappearance of the initial reactant and the reduction of the intermediates.

After the addition of 50 cm³ of ethyl acetate to destroy the excess hydride, the solution is poured into 200 cm³ of water, acidified with 3N HCl and extracted with ethyl acetate. The organic phases are washed, dried on magnesium sulfate and concentrated under reduced pressure.

6 g of 1-(2,4-diisopropyl phenyl)-1(4hydroxymethyl phenyl) methanol are recovered which crystallizes in hexane in the form of a white powder melting at 85°-86° C. and whose NMR¹H spectrum 80 MHz conforms to the expected structure

Example 22

Preparation of 4-[(2,4-diisopropyl phenyl) hydroxymethyl]benzoic acid

Compound of formula IV wherein
$R'_2 = R'_4 = $ iso $C_3H_7$, R' = H, R" = OH, $R'_3 = R'_5 = H$ and $R'_1 = -CO_2H$ To a solution, stirred at ambient temperature, of lg of 4-(2,4-diisopropyl benzoyl) benzoic acid obtained in Example 20 in 100 cm³ of methanol there are added, in small portions, 2 g of sodium borohydride.

Stirring is maintained for 2 hours until the complete disappearance of the initial reactant.

The reaction mixture is hydrolyzed with 100 cm³ of water, then acidified with a 3N solution of HCl.

After evaporation of the methanol, under reduced pressure, the aqueous phase is extracted with ethyl acetate. The organic phase is washed with water, dried on magnesium sulfate and concentrated under reduced pressure.

The residue is taken up in a small amount of diisopropyl ether and 400 mg of 4-[(2,4-diisopropyl phenyl) hydroxymethyl]benzoic acid melting at 114°-115° C. are obtained.

The NMR¹H spectrum 80 MHz conforms to the expected structure.

Example 23

Preparation of 4-(2,4-diisopropyl benzoyl) benzaldehyde

Compound of formula IV wherein
$R'_2 = R'_4 = $ iso $C_3H_7$, R' and R" = oxo, $R'_3 = R'_5 = H$ and $R'_1 = -CHO$.

To a solution of 6 g of 1-(2,4-diisopropyl phenyl)-1-(4-hydroxymethyl phenyl) methanol, obtained in Example 21, in 200 cm³ of anhydrous dichloromethane 10.8 g of pyridinium chlorochromate are added.

Stirring is maintined for about 3 hours until the complete disappearances of the initial reactant. After the addition of about 20 grams of silica and 300 cm³ of dichloromethane, the solution is filtered, washed with a solution of ammonium chloride and water, dried on magnesium sulfate and concentrated under reduced pressure.

After purification by silica gel chromatography (eluant, 9/1 hexane/ethyl acetate) 3 g of 4-(2,4-diisopropyl benzoyl) benzaldehyde in the form of an oil are recovered.

The NMR¹H spectrum 80 MHz conforms to the expected structure.

Example 24

Preparation of 4-(2,4-diisopropyl benzoyl) o-methyl ethyl cinnamate

Compound of formula I wherein n=1,
$R_2=R_4=$iso $C_3H_7$, $R'$ and $R''=$oxo, $R_3=R_5=R_6=R_7=R_8=$H, $R_9=CH_3$ and $R_1=-CO_2C_2H_5$.

To a solution of 3.5 cm³ of 2-triethyl phosphono propionate in 200 cm³ of anhydrous tetrahydrofuran there is added in small portions, 1 g of sodium hydride. A gaseous evolution is observed.

Stirring is maintained for about 2 hours, then in the absence of light, a few drops of ring ether are added and a solution of 3 g of 4-(2,4-diisopropyl benzoyl) benzaldehyde, obtained in Example 23, in solution in 50 cm³ of anhydrous tetrahydrofuran.

At the end of the addition stirring is maintained for 2 hours. The reaction mixture is then poured into a saturated solution of ammonium chloride and extracted with ethyl acetate.

The organic phases are washed, dried and concentrated under reduced pressure.

After purification by silica gel chromatography (eluant: 9.5/0.5 hexane/ethyl acetate) 29 of 4-(2,4-diisopropyl benzoyl) α-methyl ethyl cinnamate in the form of an oil whose NMRIH spectrum corresponds to the expected structure are recovered.

Example 25

Preparation of (2,4-diisopropyl benzoyl) o-methyl cinnamic acid

Compound of formula I wherein n=1,
$R_2=R_4=$iso $C_3H_7$, $R'$ and $R''=$oxo,
$R_3=R_5=R_6=R_7=R_8=$H, $R_9=CH_3$ and $R_1=-CO_2H$ A solution of 1.5 g of 4-(2,4-diisopropyl benzoyl) a-methyl ethylcinnamate, obtained in Example 24, is stirred for 2 hours in a mixture of 100 cm³ of ethanol and 50 cm³ of 6N aqueous potash at a temperature between 40 and 50° C.

After evaporation of the ethanol under reduced pressure, the residue is taken up in 500 cm³ of water and acidified with 3N HCl.

The expected acid is extracted with ethyl acetate. The organic phases are washed, dried and concentrated under reduced pressure.

On recrystallization in hexane 0.9 g of a white powder melting at 119°-120° C. is obtained. The NMR¹H spectrum 80 MHz corresponds to the structure of 4-(2,4-diisopropyl benzoyl) α-methyl cinnamic acid.

Elemental Analysis: $C_{23}H_{26}O_3$.

|  | C % | H % | O % |
| --- | --- | --- | --- |
| Calculated: | 78.82 | 7.48 | 13.70 |
| Found: | 79.91 | 7.49 | 13.90 |

Example 26

Preparation of 4-[(3-adamantyl-4-methoxy phenyl) hydroxymethyl]methyl benzoate Compound of formula IV whrein $R'_1=-CO_2CH_3$, $R'=$H, $R''=$OH, $R'_5=$adamantyl, $R'_4=$OCH$_3$, $R'_2=R'_3=$H.

A solution of 38 g (0.118 mole) of 2-adamantyl-4-bromo anisole in 350 cm³ of tetrahydrofuran is added to 2.87 g (0.118 mole) of magnesium. Reflux of tetrahydrofuran is maintained until the complete disappearance of the magnesium. After having cooled the reaction mixture to 0° C. there is slowly added a solution of 13.7 g of methyl 4-formyl benzoate in 50 cm³ of tetrahydrofuran. The mixture is maintained for 1 hour at ambient temperature, then poured into a saturated solution of ammonium chloride. The expected product is extracted with ether.

The organic phases are washed, dried on magnesium sulfate and concentrated under reduced pressure.

After chromatography on silica gel under pressure (eluant: 95/5 toluene/ethyl acetate) 19 g of a white crystallized product melting at 109–110° C. are recovered. The NMR¹H spectrum 80MHz corrresponds to the structure of 4-[(3-adamanthyl-4methoxy phenyl) hydroxymethyl]methyl benzoate.

Example 27

Preparation of 4-[(3-adamantyl-4-methoxy phenyl) hydroxymethyl]benzoic acid

Compound of formula IV wherein $R'_1=-CO_2H$, $R'=R'_2=R'_3=$H, $R''=$OH, $R'_5=$adamantyl A suspension of 19 g of 4-[(3-adamantyl-4-methoxy phenyl) hydroxymethyl]methylbenzoate, obtained in Example 26, is heated for 1 hour 30 minutes at 60° C. in a mixture of 300 cm³ of ethanol and 200 cm³ of 6N aqueous potash.

After evaporation of the ethanol under reduced pressure, the residue is taken up in 300 cm³ of water and acidified to pH 2 with 3N HCl.

The expected acid is extracted with ether. The organic phases are washed, dried and concentrated under reduced pressure.

17 g of a slightly cream colored product melting at 219°-220° C. are recovered. The NMR¹H spectrum 80MHz corresponds to the structure of 4-[(3-adamantyl-4-methoxy phenyl) hydroxymethyl]benzoic acid Elemental Analysis: $C_{25}H_{28}O_4$.

|  | C % | H % | O % |
| --- | --- | --- | --- |
| Calculated: | 76.50 | 7.19 | 16.31 |
| Found: | 76.17 | 7.08 | 15.93 |

Example 28

Preparation of 4-(3-adamantyl-4-methoxy benzoyl) benzoic acid

Compound of formula IV wherein
$R'_1=CO_2H$, $R'_2=R'_3=$H, $R'$ and $R''=$oxo, $R'_5=$adamantyl and $R'_4=$OCH$_3$ To the solution of 10 g of 4-[(3-adamantyl-4-methoxy phenyl) hydroxymethyl]benzoic acid, obtained in Example 27, in 700 cm³ of acetone, there are slowly added, at ambient temperature, a solution of 8 g of $K_2Cr_2O_7$, 7 cm³ of concentrated sulfuric acid and 50 cm³ of water.

Stirring is maintained for 1 hour until the disappearance of the initial reactant.

After evaporation under reduced pressure of the acetone, the residue is taken up in 500 cm³ of water and extracted with ethyl ether.

The organic phases are washed, dried on magnesium sulfate and concentrated under reduced pressure. 9.5 g of 4-(3-adamantyl-4-methoxy benzoyl) benzoic acid are recovered. The NMR¹H spectrum 80MHz corresponds to the expected structure.

2.5 g of the acid whose melting point is 235°–236° C. are recovered on recrystallization of a 3 g sample of the crude acid in a toluene/hexane mixture.

Example Analysis: $C_{25}H_{26}O_4$.

|  | C % | H % | O % |
|---|---|---|---|
| Calculated: | 76.90 | 6.71 | 16.39 |
| Found: | 76.97 | 6.76 | 16.52 |

Example 29

Preparation of 4-(3-adamantyl-4-hydroxy benzoyl) methyl benzoate

Compound of formula IV wherein $R'_1=$ —$CO_2CH_3$, $R'_2=R'=H$, R' and R"=oxo, $R'_5=$adamantyl and $R'_4=OH$ To a suspension of 1.5 g of 4-(3-adamantyl-4-methoxy benzoyl) benzoic acid obtained in Example 28 in 150 cm³ of methanol, there is added 1 cm³ of a solution of concentrated HCl. The mixture is stirred for 4 hours at the boiling temperature of the solvent. Then at ambient temperature, it is poured into 200 cm³ of water, extracted three times with 100 cm³ of ethyl acetate. The ethyl acetate phases are combined, washed with water, dried on magnesium sulfate and concentrated under reduced pressure. The crude product is then fractionated by passage through a silica gel column.

The 4-(3-adamantyl-4-hydroxybenzoyl) methyl benzoate is eluted with an 8/2 hexane/ethyl acetate mixture. After evaporation of the solvent, the expected product is isolated in the form of white crystals whose melting point is 270° C.

Elemental Analysis: $C_{25}H_{26}O_4$.

|  | C % | H % | O % |
|---|---|---|---|
| Calculated: | 76.90 | 6.71 | 16.39 |
| Found: | 76.50 | 6.97 | 16.11 |

Example 30

Preparation of 4-(3,5-ditert.butyl-4-hydroxy benzoyl) methyl benzoate

Compound of formula IV wherein $R'_1=$ —$CO_2CH_3$, $R'_2=H$, R' and R"=oxo, $R'_5=tert.C_4H_9$, $R'_4=OH$.

To a solution, stirred at 0° C., containing 20 g of 2,6-di-tert.butyl phenol and 19 g of 4-methoxycarbonyl benzoic acid chloride in 300 cm³ of toluene, there are slowly added 11.6 cm³ of stannic chloride diluted with 50 cm³ of toluene. The colorless solution progressively turns red. Stirring is maintained again for 2 hours at 0° C. after the end of the addition. The reaction mixture is then left overnight at ambient temperature. The mixture is then poured into 300 cm³ of ice water and extracted three times with 150 cm³ of ethyl acetate.

The ethyl acetate phases are combined, washed with an aqueous solution of sodium bicarbonate, dried on magnesium sulfate and concentrated.

The resulting crude product is diluted in a minimum of toluene and deposited in a silica gel column. The expected product is eluted with a 1/1 mixture of hexane/ethylacetate. After evaporation of the solvent and after drying, 3 g of 4-(3,5-di-tert.butyl-4-hydroxy benzoyl)methyl benzoate in the form of a flocculent white powder whose melting point is 172° C. are obtained.

Elemental Analysis: $C_{23}H_{28}O_4$.

|  | C % | H % | O % |
|---|---|---|---|
| Calculated: | 74.97 | 7.66 | 17.37 |
| Found: | 75.00 | 7.70 | 17.52 |

Example 31

Preparation of 4-(3,5-di-tert.butyl-4-hydroxy benzoyl) benzoic acid

Compound of Example IV wherein $R'_1=$ —$CO_2H$, $R'_2=H$, R' and R"=oxo, $R'_3=R'_5=tert.C_4H_9$ and $R'_4=OH$, A solution of 1g of 4-(3,5-di-tert.butyl-4-hydroxy benzoyl) methyl benzoate, obtained in Example 30, in a mixture of 40 cm³ of a 6N aqueous potash solution and 100 cm³ of ethanol is heated for 1 hour at a temperature of 50° C. Then, the ethanol is removed by evaporation under a vacuum. The resulting product is stirred is 200 cm³ of water. The resulting solution is acidified by adding 6N HCl and then extracted with 300 cm³ of ethylacetate. The ethyl acetate phase is washed three times with water and dried on magnesium sulfate. The ethyl acetate is removed by evaporation under a vacuum. After recrystallization of the crude product in toluene in the presence of a trace of methanol, 0.7 g of 4-(3,5-di.-tert.-butyl-4-hydroxy benzoyl)benzoic acid in the form of white crystals whose melting point is 255° C. is obtained.

The NMR'H spectrum conforms to the expected structure.

Elemental Analysis: $C_{22}H_{26}O_4$.

|  | C % | H % | O % |
|---|---|---|---|
| Calculated: | 74.55 | 7.39 | 18.06 |
| Found: | 74.12 | 7.42 | 18.61 |

EXAMPLE OF COMPOSITIONS

A. Oral Compositions

Example I—0.2 g tablet

| | |
|---|---|
| 6-(4-methoxy-2,3,6-trimethyl benzoyl)-2-naphthalene carboxylic acid | 0.010 g |
| Starch | 0.115 g |
| Dicalcium phosphate | 0.020 g |
| Silica | 0.020 g |
| Lactose | 0.030 g |
| Talc | 0.010 g |
| Magnesium stearate | 0.005 g |

Example II—Drinkable suspension in 5 ml ampoules

| | |
|---|---|
| 6-(3-adamantyl-4-methoxy benzoyl)-2-naphthalene carboxylic acid | 0.010 g |
| Glycerine | 0.500 g |
| Sorbitol, 70% | 0.500 g |
| Sodium Saccharinate | 0.010 g |
| Methyl parahydroxy benzoate | 0.040 g |
| Flavoring agent, sufficient amount | |
| Purified water, sufficient amount for | 5.000 ml |

B. Topical Conditions

Example III—Ointment

| | |
|---|---|
| 6-(4-methoxy-3-phenyl benzoyl)-2-methyl naphthalene carboxylate | 0.100 g |
| Isopropyl myristate | 81.700 g |
| Fluid petrolatum oil | 9.100 g |
| Silica, sold under the trade name "Aerosil 200" by Degussa | 9.100 g |

Example IV—Anionic oil-in-water cream

| | |
|---|---|
| 6-(4-methoxy-2,3,6-trimethyl benzoyl)-2-methyl naphthalene carboxylate | 0.100 g |
| Sodium dodecyl sulfate | 0.800 g |
| Glycerol | 2.000 g |
| Stearyl alcohol | 20.000 g |
| Triglycerides of capric/caprylic acids sold under the trade name "Miglyol 812" by Dynamit Nobel | 20.000 g |
| Preservatives, sufficient amount | |
| Demineralized water, sufficient amount for | 100.000 g |

In examples III and IV above, the active compound can be replaced by an equivalent amount of 6-(2,4-diisopropyl benzoyl)-2-naphthalene carboxylic acid.

Example V—Gel

| | |
|---|---|
| N-ethyl 6-(4-tert.butyl benzoyl)-1-naphthalene carboxamide | 0.500 g |
| Hydroxypropyl cellulose sold under the trade name "Klucel HF" by Hercules | 2.000 g |
| Water/ethanol, 50/50, sufficient amount for | 100.000 g |

Example VI—Anti-seborrhea cream

| | |
|---|---|
| Polyoxyethylenated stearate (40 moles of ethylene oxide), sold under the trade name "Myrj 52" by Atlas | 4.00 g |
| Mixture of lauryl esters of sorbitol and sorbitan, polyoxyethylenated with 20 moles of ethylene oxide, sold under the trade name "Tween 20" by Atlas | 1.800 g |
| Mixture of glycerol mono- and di-stearate, sold under the trade name "GELEOL" by Gattefosse | 4.200 g |
| Propylene glycol | 10.000 g |
| Butyl hydroxyanisole | 0.010 g |
| Butyl hydroxytoluene | 0.020 g |
| Cetyl-stearyl alcohol | 6.200 g |
| Preservatives, sufficient amount | |
| Perhydrosqualene | 18.000 g |
| Mixture of caprylic-capric triglycerides, sold under the trade name "Miglyol 812" by Dynamit Nobel | 4.000 g |
| S-carboxymethyl cysteine | 3.000 g |
| Triethanolamine, 99% | 2.500 g |
| 6-(2,4-diisopropyl benzoyl)-2-naphthalene carboxylic acid | 0.100 g |
| Water, sufficient amount for | 100.000 g |

Example VII—Anti-seborrhea cream

| | |
|---|---|
| Stearate polyoxyethylenated (40 moles of ethylene oxide), sold under the trade name "Myrj 52" by Atlas | |
| Mixture of lauryl esters of sorbitol and sorbitan, polyoxyethylenated with 20 moles of ethylene oxide, sold under the trade name "Tween 20" by Atlas | 1.800 g |
| Mixture of mono- and distearate of glycerol, sold under the trade name "GELEOL" by Gattefosse | 4.200 g |
| Propylene glycol | 10.000 g |
| Butylhydroxyanisole | 0.010 g |
| Butylhydroxytoluene | 0.020 g |
| Cetyl-stearyl alcohol | 6.200 g |
| Preservatives, sufficient amount | |
| Perhydrosqualene | 18.000 g |
| Mixture of caprylic-capric triglycerides, sold under the trade name "Miglyol 812" by Dynamit Nobel | 4.000 g |
| 5-amino-5-carboxy-3-thiapentanoate of 2-benzylthio ethylammonium | 3.000 g |
| 6-(4-tert.butyl benzoyl)-2-naphthalene carboxylic acid | 0.500 g |
| Water, sufficient amount for | 100.000 g |

Example VIII—Hair lotion

| | |
|---|---|
| Propylene glycol | 20.000 g |
| Ethanol | 34.870 g |
| Polyethylene glycol, molecular mass 400 | 40.000 g |
| Water | 4.000 g |
| Butylhydroxyanisole | 0.010 g |
| Butylhydroxytoluene | 0.020 g |
| 6-(3-adamantyl-4-methoxy benzoyl)-2-naphthalene carboxylic acid | 0.100 g |
| Minoxidil | 1.000 g |

Example IX—Anti-acne gel

| | |
|---|---|
| 6-(2,4-diisopropyl benzoyl)-2-naphthalene carboxylic acid | 0.200 g |
| Isopropyl alcohol | 40.000 g |
| Polymer of acrylic acid, sold under the trade name "CARBOPOL 940" by Goodrich Chemical Co. | 1.000 g |
| Triethanolamine, 99% | 0.600 g |
| Butylhydroxyanisole | 0.010 g |
| Butylhydroxytoluene | 0.020 g |
| Tioxolone | 0.500 g |
| Propylene glycol | 8.000 g |
| Purified water, sufficient amount for | 100.000 g |

What is claimed is:

1. An aromatic compound having the formula

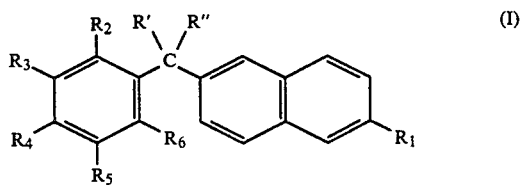

(I)

wherein

R' represents hydrogen or alkoxy having 1–4 carbon atoms,

R" represents hydrogen, OH, acyloxy having 1–4 carbon atoms, alkoxy having 1–4 carbon atoms, or NH$_2$, or R' and R" taken together form an oxo, methano or hydroxyimino radicla, R$_1$ represents —CH$_2$OH or —COR$_{10}$, R$_{10}$ represents hydrogen, —OR$_{11}$ or $$-N\begin{matrix}r'\\r''\end{matrix},$$

R$_{11}$ represents hydrogen, linear or branched alkyl having 1–20 carbon atoms, monohydroxyalkyl, polyhydroxyalkyl, aryl or aralkyl optionally substituted, the residue of a sugar or $$-(CH_2)_p-N\begin{matrix}r'\\r''\end{matrix}$$

wherein p is 1,2 or 3 and r' and r" represent hydrogen, lower alkyl, monohydroxyalkyl optionally interrupted by a heteroatom, polyhydroxyalkyl, aryl or benzyl optionally substituted, the residue of an amino acid, the residue of an aminated sugar, or r' and r" taken together form a heterocycle, R$_2$, R$_3$, R$_4$, R$_5$ and R$_6$ represent hydrogen, —OH, linear or branched alkyl having 1–12 carbon atoms, cycloalkyl, cycloalkenyl, phenyl optionally substituted or a radical selected from (i) —X—C$_6$H$_5$, (ii) —X—R$_{12}$ or (iii) —NHCOR$_{13}$, wherein X represents —O—, —S—, —SO—, —SO$_2$— or —OCO—, R$_{12}$ represents alkyl or lower fluoroalkyl and R$_{13}$ represents alkyl or phenyl, at least one of R$_2$ to R$_6$ being other than hydrogen, and the salts of said aromatic compound or its optical and geometric isomers.

2. The compound of claim 1 wherein said lower alkyl radical and said alkyl radical having up to 20 carbon atoms are selected from the group consisting of methyl, ethyl, isopropyl, butyl, tert. butyl, isooctyl, dodecyl, hexadecyl and octadecyl.

3. The compound of claim 1 wherein said monohydroxyalkyl has 2–6 carbon atoms.

4. The compound of claim 1 wherein said monohydroxyalkyl is 2-hydroxyethyl, 2-hydroxypropyl or 2-hydroxyethoxyethyl.

5. The compound of claim 1 wherein said polyhydroxyalkyl has 3–6 carbon atoms and 2–5 hydroxyl groups.

6. The compound of claim 5 wherein said polyhydroxyalkyl is 2,3-dihydroxypropyl, 1,3-dihydroxypropyl or the residue of pentaerythritol.

7. The compound of claim 1 wherein said aryl is phenyl or phenyl substituted by halogen, —OH, —NO$_2$, lower alkyl, trifluoromethyl or a carboxylic acid function.

8. The compound of claim 1 wherein said aralkyl is benzyl or phenethyl.

9. The compound of claim 1 wherein said residue of a sugar is derived from glucose, mannose, erythrose or galactose.

10. The compound of claim 1 wherein said residue of an aminated sugar is derived from glucosamine, galactosamine or mannosamine.

11. The compound of claim 1 wherein said cycloalkyl is cyclopentyl, cyclohexyl or adamantyl.

12. The compound of claim 1 wherein said cycloalkenyl is cyclohexen-1 yl or cyclopenten-1 yl.

13. The compound of claim 1 wherein r' and r" taken together form piperidino, piperazino, morpholino, pyrrolidino or 4-(2-hydroxyethyl) piperazino.

14. The compound of claim 1 having the formula wherein

R'$_{10}$ represents —OR'$_{11}$ or —NHR'$_{11}$ wherein R'$_{11}$ represents hydrogen or lower alkyl, R'$_2$ represents hydrogen or lowe alkyl, and R"$_4$ represents lower alkyl.

15. The compound of claim 14 wherein R"$_4$ represents isopropyl, tert.butyl or cyclohexyl.

16. The compound of claim 1 having the formula wherein

R'$_{10}$ represents —OR'$_{11}$ or —NHR'$_{11}$ wherein R'$_{11}$ represents hydrogen or lower alkyl, R"$_2$ and R'$_6$ represent hydrogen or lower alkyl, R'$_3$ represents hydrogen, lower alkyl, phenyl or adamantyl, and R'$_{12}$ represents lower alkyl or phenyl.

17. The compound of claim 1 selected from the group consisting of (1) 6-(2,4-diisopropyl benzoyl) 2-methyl naphthalene carboxylate, (2) 6-(2,4-diisopropyl benzoyl) naphthalene carboxylic acid, (3) 6-(4-methoxy-2,3,6-trimethyl benzoyl)-2-methyl naphthalene carboxylate, (4) 6-(4-methoxy -2,3,6-trimethyl benzoyl)-2-naphthalene carboxylic acid, (5) 6-(4-tert.butyl benzoyl)-2-methyl naphthalene carboxylate, (6) 6-(4-tert.butyl benzoyl)-2-naphthalene carboxylic acid, (7) N-ethyl 6-(4-tert.butyl benzoyl)-2-naphthalene carboxamide, (8) 6-(3-adamantyl-4-methoxy benzoyl)-2-naphthalene carboxylate, (9) 6-(3-adamantyl-4-methoxy benzoyl)-2-naphthalene carboxylic acid,

(10) 6-(4-methoxy benzoyl)-2-methyl naphthalene carboxylate,

(11) 6-(4-cyclohexyl benzoyl)-2-methyl naphthalene carboxylate,

(12) 6-(4-cyclohexyl benzoyl)-2-naphthalene carboxylic acid,

(13) 6-(4-methoxy-3-phenyl benzoyl)-2-methyl naphthalene carboxylate,

(14) 6-(4-methoxy-3-phenyl benzoyl)-2-naphthalene carboxylic acid,

(15) 6-(4-phenoxy benzoyl)-2-methyl naphthalene carboxylate,
(16) 6-[(2,4-diisopropyl phenyl) hydroxymethyl]-2-naphthalene carboxylic acid,
(17) 6-[(2,4-diisopropyl phenyl) hydroxymethyl]-2-naphthalene carbinol, and
(18) 6-(2,4-diisopropyl benzyl-2naphthalene carboxylic acid.

18. A pharmaceutical composition comprising in a pharmaceutically acceptable carrier suitable for enteral, parenteral, topical or ocular administration, an effective amount of at least one compound of claim 1.

19. The pharmaceutical composition of claim 18 wherein said carrier is suitable for topical or ocular administration and said compound is present in an amount ranging from 0.0005 to about 5 percent by weight of said composition.

20. A cosmetic composition for body and hair hygiene comprising in a cosmetically acceptable vehicle an effective amount of at least one compound of claim 1.

21. The cosmetic composition of claim 20 wherein said compound is present in an amount ranging from 0.0005 to 2 percent by weight of said composition.

22. The cosmetic composition of claim 20 wherein said compound is present in an amount ranging from 0.01 to 1 percent by weight of said composition.

* * * * *